United States Patent [19]

Shiokawa et al.

[11] Patent Number: 4,774,247
[45] Date of Patent: Sep. 27, 1988

[54] NITROMETHYLENE DERIVATIVE INSECTICIDES

[75] Inventors: Kozo Shiokawa, Kanagawa; Shinichi Tsuboi, Tokyo; Shinzo Kagabu, Tokyo; Koichi Moriya, Tokyo, all of Japan

[73] Assignee: Nihon Tokushu Noyaku Seizo K.K., Tokyo, Japan

[21] Appl. No.: 29,303

[22] Filed: Mar. 23, 1987

Related U.S. Application Data

[62] Division of Ser. No. 720,838, Apr. 8, 1985, Pat. No. 4,678,795.

[30] Foreign Application Priority Data

Apr. 13, 1984 [JP] Japan .................................. 59-72966
Jun. 29, 1984 [JP] Japan ................................ 59-132943

[51] Int. Cl.⁴ ..................... A01N 43/54; C07D 401/00
[52] U.S. Cl. ..................................... 514/256; 544/333
[58] Field of Search ......................... 544/333; 514/256

[56] References Cited

U.S. PATENT DOCUMENTS 4,136,188  1/1979  Ishikawa et al. .................... 544/333

Primary Examiner—Alan L. Rotman
Assistant Examiner—Robert C. Whittenbaugh
Attorney, Agent, or Firm—Sprung Horn Kramer & Woods

[57] ABSTRACT

Novel insecticides of the formula

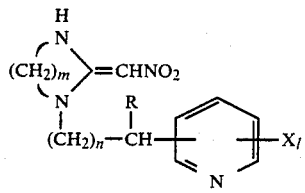

in which
R is a hydrogen atom or a lower alkyl group,
X is a halogen atom, a lower alkyl group, a lower alkoxy group, a lower alkylthio group, a lower alkylsulfinyl group, a lower alkylsulfonyl group, a lower alkenyl group, a lower alkynyl group, an aryl group, an aryloxy group which may be optionally substituted by a halogen atom, an arylthio group which may be optionally substituted by a halogen atom, or an aralkyl group,
$l$ is 1, 2, 3 or 4,
$m$ is 2, 3 or 4, and
$n$ is 0, 1, 2 or 3,
or salts thereof. Intermediates therefor of the formula

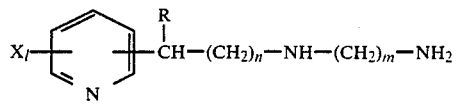

are also new.

9 Claims, No Drawings

NITROMETHYLENE DERIVATIVE INSECTICIDES

This is a division of application Ser. No. 720,838, filed Apr. 8, 1985, now U.S. Pat. No. 4,678,795, issued July 7, 1987.

This invention relates to novel nitromethylene derivatives, intermediates thereof, processes for production thereof, and insecticides containing said novel nitromethylene derivatives as active ingredients.

More specifically, this invention relates to novel nitromethylene derivatives represented by the following general formula (I):

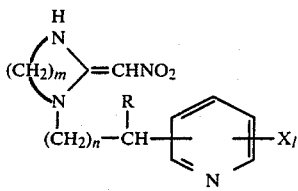

wherein
R represents a hydrogen atom or a lower alkyl group,
X represents a halogen atom, a lower alkyl group, a lower alkoxy group, a lower alkylthio group, a lower alkylsulfinyl group, a lower alkylsulfonyl group, a lower alkenyl group, a lower alkynyl group, an aryl group, an aryloxy group which may be optionally substituted by a halogen atom, an arylthio group which may be optionally substituted by a halogen atom, or an aralkyl group,
l represents 1, 2, 3 or 4,
m represents 2, 3 or 4, and
n represents 0, 1, 2 or 3.

It has to be stated that in case l>1, the radicals X may be the same or different from each other.

The nitromethylene derivatives of formula (I) in accordance with this invention can be produced by the following process (i) to which the invention also pertains:

Process (i)
A process for producing the nitromethylene derivatives of general formula (I), which comprises reacting a compound represented by the general formula

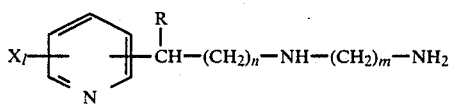

wherein R, X, l, m and n are as defined above, with a compound represented by the general formula

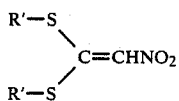

wherein each
R' represents a lower alkyl group, a benzyl group or the two R' groups together represent a lower alkylene group having at least 2 carbon atoms and may form a ring together with the sulfur atoms adjacent thereto.

This invention also relates to insecticides comprising the nitromethylene derivative of general formula (I) as an active ingredient.

In the production of the novel nitromethylene derivatives of general formula (I) in accordance with this invention, the compound of general formula (II), an intermediate, is a novel compound which is not described in any known publication, and the present invention also relates to said compounds (intermediates).

The novel compound of general formula (II) can be produced by the following process (ii) to which the invention also pertains:

Process (ii)
A process for producing the compound of general formula (II), which comprises reacting a compound represented by the general formula

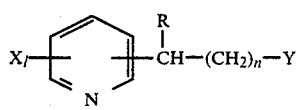

wherein
R, X, l, and n are as defined above, and
Y represents a halogen atom or the group —OSO$_2$R" in which R" represents a lower alkyl or an aryl group, with a compound represented by the general formula $$H_2N-(CH_2)_m-NH_2 \quad (V)$$

wherein m is as defined above.

Compounds of general formula (IV) are either known or can be produced by known preparation methods.

German Offenlegungsschrift No. 2,514,402 known before the filing date of the present application states that 2-nitromethylene-imidazolidine derivatives and 2-nitromethylenehexahydropyrimidine derivatives of the following general formula

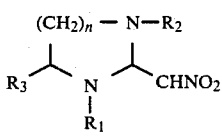

have insecticidal activity. The above general formula includes cases of n=2, R$_1$=phenyl-(C$_1$-C$_2$)alkyl group and R$_2$=R$_2$=hydrogen and the specification of the above German patent document describes a compound of the following formula

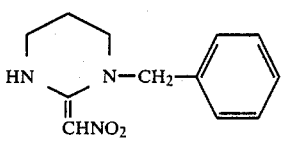

German Offenlegungsschrift No. 2,732,660 states that 1-substituted benzyl-2-nitromethylene-imidazolidine derivatives represented by the following general formula

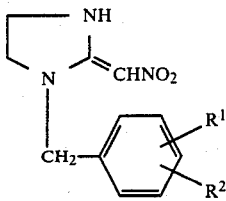

have insecticidal activity. The specification of this German Offenlegungsschrift describes a compound represented by the following formula.

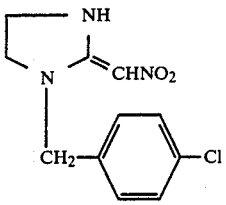

(B-1)

It has been found that the compounds of this invention in low dosages have superior controlling activity relative to the compounds of formulae (A-1) and (B-1) which are described in the above-cited German Offenlegungsschriften and are most similar to the compounds of this invention, and that the compounds of this invention exhibit a marked controlling effect against noxious insects which have acquired resistance to organic phosphate and carbamate type insecticides through long-term use, particularly sucking insects typified by hemipterous insects such as aphids, planthoppers and leafhoppers.

The active compounds of this invention exhibit an accurate controlling effect against noxious insects, without causing any phytotoxicity to cultivated plants. Furthermore, the compounds of this invention can be used for control and eradication of a wide range of pests, including sucking insects, biting insects and other plant parasites, pests on stored grains and pests causing health hazards.

Examples of the pests are shown below.

COLEOPTEROUS INSECTS

Callosobruchus chinensis,
Sitophilus zeamais,
Tribolium castaneus,
Epilachna vigitoctomaculata,
Agriotes fuscicollis,
Anomala rufocuprea,
Leptinotarsa decemkineata,
Diabrotica spp.,
Monochamus alternatus,
Lissorhoptrus oryzophilus, and
Lyctus brunneus.

LEPIDOPTEROUS INSECTS

Lymantria dispar,
Malacosoma neustria,
Pieris rapae,
Spodoptera litura,
Mamestra brassicae,
Chilo suppressalis,
Pyrausta nubilalis,
Ephestia cautella,
Adoxophyes orana,
Carpocapsa pomonella,
Agrotis fucosa,
Galleria mellonella,
Plutella maculipennis, and
Phyllocnistis citrella.

HEMIPTEROUS INSECTS

Nephotettix cincticeps,
Nilaparvata lugens,
Pseudococcus cometocki,
Unaspis yanonensis,
Myzus persicae,
Aphis pomi,
Aphis gossypii,
Rhopalosiphum pseudobrassicas,
Stephanitis nashi,
Nazara spp.,
Cimex lectularius,
Trialeurodes vaporariorum, and
Psylla spp.

ORTHOPTEROUS INSECTS

Blatella germanica,
Periplaneta americana,
Cryllotalpa africana, and
Locusta migratoria migratoriodes.

ISOPTEROUS INSECTS

Deucotermes speratus, and
Coptotermes formosanus.

DIPTEROUS INSECTS

Musca domestica,
Aedes aegypti,
Hylemia platura,
Culex pipens,
Anopheles sinensis, and
Culex tritaeniorhynchus.

In the field of veterinary medicine, the novel compounds of this invention are effective against various noxious animal parasites (endo- and ecto-parasites) such as insects and worms. Examples of such animal parasites are shown below.

INSECTS

Gastrophilus spp.,
Stomoxys spp.,
Trichodectes spp.,
Rhodnius spp., and
Ctenocephalides canis.

Substances having pesticidal activity against all of these pests may sometimes be referred to in this application simply as insecticides.

The nitromethylene derivative of general formula (I) in accordance with this invention can be easily produced, for example, by the following process (i):

Process (i)

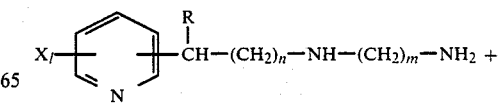

(II)

-continued

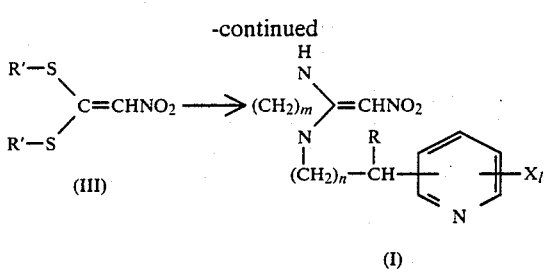

(In the formulae, R, X, l, m, n and R' are as defined hereinabove.)

In the above reaction scheme, R represents a hydrogen atom or a lower alkyl group, and specific examples of a lower alkyl group may include methyl, ethyl, propyl, isopropyl and n-(iso-, sec- or tert-)butyl.

X represents halogen atom, a lower alkyl group with preferably 1 to 6 carbon atoms, a lower alkoxy group, a lower alkylthio group with preferably 1 to 6 carbon atoms, a lower alkylsulfinyl group with preferably 1 to 6 carbon atoms, a lower alkylsulfonyl group with preferably 1 to 6 carbon atoms, a lower alkenyl group with preferably 2 to 6 carbon atoms, a lower alkynyl group with preferably 2 to 4 carbon atoms, an aryl group with preferably 6 or 10 ring carbon atoms, an aryloxy group which may be optionally substituted by a halogen atom, an arylthio group which may be optionally substituted by a halogen atom, or an aralkyl group, and specific examples of a halogen atom may include fluoro, chloro, bromo and iodo, specific examples of a lower alkyl are the same as those exemplified above, specific examples of a lower alkoxy group, a lower alkylthio group, a lower alkylsufinyl group and a lower alkylsulfonyl group may be respectively those having the same lower alkyl group as exemplified above, specific examples of a lower alkenyl may include vinyl, allyl, 1-propenyl or 1-(2- or 3-)butenyl, specific examples of a lower alkynyl may include ethynyl, 1-propynyl or propargyl, specific examples of an aryl group may include phenyl or α-(or β-) naphthyl, specific examples of an aryloxy group and an arylthio group which may be optionally substituted by a halogen atom may be respectively those having the same aryl group as exemplified above which may be substituted by one or two halogen atom(s) such as exemplified above, and specific examples of an aralkyl group may include benzyl, phenethyl or α-naphthylmethyl.

l represents 1, 2, 3 or 4.
m represents 2, 3 or 4.
n represents 0, 1, 2 or 3.
R' represents a lower alkyl group with preferably 1 to 6 carbon atoms, a benzyl group, or the two R' groups together represent a lower alkylene group having at least 2 carbon atoms. Specific examples of the lower alkyl group are the same as those exemplified above for R. The two R' groups together may represent a lower alkylene group having at least 2 carbon atoms and may form a ring together with the sulfur atoms adjacent thereto. An ethylene group may be cited as an example of such an alkylene group.

In the process for producing the compounds of general formula (I) of this invention represented by the reaction scheme, specific examples of the starting compound of general formula (II) include II-1. N-(5-methyl-2-pyridylmethyl)ethylenediamine,
II-2. N-(5-methyl-2-pyridylmethyl)trimethylenediamine,
II-3. N-(6-methyl-2-pyridylmethyl)ethylenediamine,
II-4. N-(6-methyl-2-pyridylmethyl)trimethylenediamine,
II-5. N-(4-methyl-2-pyridylmethyl)ethylenediamine,
II-6. N-(4-methyl-2-pyridylmethyl)trimethylenediamine,
II-7. N-(5-ethyl-2-pyridylmethyl)ethylenediamine,
II-8. N-(5-buthyl-2-pyridylmethyl)ethylenediamine,
II-9. N-(4,6-dimethyl-2-pyridylmethyl)ethylenediamine,
II-10. N-(3-chloro-2-pyridylmethyl)ethylenediamine,
II-11. N-(5-chloro-2-pyridylmethyl)ethylenediamine,
II-12. N-(5-chloro-2-pyridylmethyl)trimethylenediamine,
II-13. N-(3,5-dichloro-2-pyridylmethyl)ethylenediamine,
II-14. N-(5-fluoro-2-pyridylmethyl)trimethylenediamine,
II-15. N-(6-bromo-2-pyridylmethyl)ethylenediamine,
II-16. N-[2-(5-ethyl-2-pyridyl)ethyl]trimethylenediamine,
II-17. N-(6-chloro-4-methyl-2-pyridylmethyl)ethylenediamine,
II-18. N-(5-methyl-3-pyridylmethyl)ethylenediamine,
II-19. N-(2-methyl-5-pyridylmethyl)ethylenediamine,
II-20. N-(2-methyl-5-pyridylmethyl)trimethylenediamine,
II-21. N-(2-phenyl-5-pyridylmethyl)ethylenediamine,
II-22. N-(2-phenyl-5-pyridylmethyl)trimethylenediamine,
II-23. N-(2-benzyl-5-pyridylmethyl)ethylenediamine,
II-24. N-(2-chloro-3-pyridylmethyl)ethylenediamine,
II-25. N-(2-chloro-3-pyridylmethyl)trimethylenediamine,
II-26. N-(5-chloro-3-pyridylmethyl)ethylenediamine,
II-27. N-(5-chloro-3-pyridylmethyl)trimethylenediamine,
II-28. N-(5-bromo-3-pyridylmethyl)ethylenediamine,
II-29. N-(5-bromo-3-pyridylmethyl)trimethylenediamine,
II-30. N-(2-bromo-5-pyridylmethyl)ethylenediamine,
II-31. N-(2-bromo-5-pyridylmethyl)trimethylenediamine,
II-32. N-(5-fluoro-3-pyridylmethyl)ethylenediamine,
II-33. N-(2-fluoro-5-pyridylmethyl)ethylenediamine,
II-34. N-(2-fluoro-5-pyridylmethyl)trimethylenediamine,
II-35. N-[1-(2-fluoro-5-pyridyl)ethyl]ethylenediamine,
II-36. N-[2-methyl-1-(2-fluoro-5-pyridyl)propyl]ethylenediamine,
II-37. N-[2-(2-fluoro-5-pyridyl)ethyl]ethylenediamine,
II-38. N-[3-(2-bromo-5-pyridyl)propyl]trimethylenediaine,
II-39. N-(2-bromo-5-pyridylmethyl)tetramethylenediamine,
II-40. N-[4-(2-bromo-5-pyridyl)butyl]trimethylenediamine,
II-41. N-(2-chloro-6-methyl-3-pyridylmethyl)ethylenediamine,
II-42. N-(2,4-dichloro-5-pyridylmethyl)trimethylenediamine,
II-43. N-(2,6-dichloro-3-pyridylmethyl)ethylenediamine,
II-44. N-(2,4-dibromo-5-pyridylmethyl)ethylenediamine, II-45. N-(2,4-difluoro-5-pyridylmethyl)ethylenediamine,
II-46. N-(2,4,5,6-tetrafluoro-3-pyridylmethyl)ethylenediamine,
II-47. N-(2,4,5,6-tetrachloro-3-pyridylmethyl)ethylenediamine,
II-48. N-(2-methoxy-3-pyridylmethyl)trimethylenediamine,
II-49. N-(2-methoxy-5-pyridylmethyl)ethylenediamine,
II-50. N-(2-methoxy-5-pyridylmethyl)trimethylenediamine,
II-51. N-(2-ethoxy-5-pyridylmethyl)ethylenediamine,
II-52. N-(2-ethoxy-5-pyridylmethyl)trimethylenediamine,
II-53. N-(2-iso-propoxy-5-pyridylmethyl)ethylenediamine,
II-54. N-(2-phenoxy-5-pyridylmethyl)ethylenediamine,
II-55. N-(2-phenoxy-5-pyridylmethyl)trimethylenediamine,
II-56. N-[2-(2,4-dichlorophenoxy)-5-pyridylmethyl]ethylenediamine,
II-57. N-(2-methylthio-3-pyridylmethyl)ethylenediamine,
II-58. N-(2-methylthio-5-pyridylmethyl)ethylenediamine,
II-59. N-(2-methylthio-5-pyridylmethyl)trimethylenediamine,
II-60. N-(4-methyl-2-methylthio-5-pyridylmethyl)ethylenediamine,
II-61. N-(2-phenylthio-5-pyridylmethyl)ethylenediamine,
II-62. N-[2-(4-chlorophenylthio)-5-pyridylmethyl]ethylenediamine,
II-63. N-(2-ethylthio-5-pyridylmethyl)ethylenediamine,
II-64. N-(2-methylsulfinyl-5-pyridylmethyl)ethylenediamine,
II-65. N-(2-methylsulfonyl-5-pyridylmethyl)trimethylenediamine,
II-66. N-(4-chloro-2-fluoro-5-pyridylmethyl)trimethylenediamine,
II-67. N-(6-chloro-2-methyl-3-pyridylmethyl)ethylenediamine,
II-68. N-(2-chloro-4-methyl-5-pyridylmethyl)ethylenediamine,
II-69. N-(2-allyl-5-pyridylmethyl)ethylenediamine,
II-70. N-(2-propargyl-5-pyridylmethyl)ethylenediamine,
II-71. N-(2,3-dichloro-5-pyridylmethyl)ethylenediamine,
II-72. N-[2-(1-propenyl)-5-pyridylmethyl]ethylenediamine,
II-73. N-(2-chloro-4-pyridylmethyl)ethylenediamine,
II-74. N-(2-chloro-4-pyridylmethyl)trimethylenediamine,
II-75. N-(2-fluoro-4-pyridylmethyl)ethylenediamine,
II-76. N-(2-fluoro-4-pyridylmethyl)trimethylenediamine,
II-77. N-(2,6-dichloro-4-pyridylmethyl)ethylenediamine,
II-78. N-(2,6-difluoro-4-pyridylmethyl)trimethylenediamine,
II-79. N-(2-methyl-4-pyridylmethyl)ethylenediamine,
II-80. N-(2-methyl-4-pyridylmethyl)trimethylenediamine,
II-81. N-[1-(2-chloro-4-pyridyl)ethyl]ethylenediamine,
II-82. N-(2-chloro-6-methyl-4-pyridylmethyl)ethylenediamine,
II-83. N-(2-chloro-6-methyl-4-pyridylmethyl)trimethylenediamine,
II-84. N-(2,6-dimethyl-4-pyridylmethyl)ethylenediamine,
II-85. N-(2-bromo-4-pyridylmethyl)ethylenediamine,
II-86. N-(2,6-dibromo-4-pyridylmethyl)ethylenediamine,
II-87. N-(2,3,5,6-tetrafluoro-4-pyridylmethyl)ethylenediamine,
II-88. N-(2,3,5,6-tetrafluoro-4-pyridyl)trimethylenediamine,
II-89. N-(2,6-dichloro-4-pyridylmethyl)trimethylenediamine,
II-90. N-(3-chloro-2-fluoro-5-pyridylmethyl)ethylenediamine,
II-91. N-(3-bromo-2-fluoro-5-pyridylmethyl)ethylenediamine,
II-92. N-(2-chloro-3-fluoro-5-pyridylmethyl)ethylenediamine,
II-93. N-(2,3,4-trichloro-5-pyridylmethyl)ethylenediamine,
II-94. N-(3-chloro-2-methylthio-5-pyridylmethyl)ethylenediamine,
II-95. N-(2-chloro-5-pyridylmethyl)ethylenediamine,
II-96. N-[2-(2-chloro-5-pyridyl)ethyl]ethylenediamine,
II-97. N-(2-chloro-5-pyridylmethyl)trimethylenediamine,
II-98. N-[2-(2-chloro-5-pyridyl)ethyl]trimethylenediamine,
II-99. N-[1-(2-chloro-5-pyridyl)ethyl]trimethylenediamine,
II-100. N-[3-(2-chloro-5-pyridyl)propyl]trimethylenediamine,
II-101. N-[1-(2-chloro-5-pyridyl)ethyl]ethylenediamine,
II-102. N-2-chloro-5-pyridylmethyl)tetramethylenediamine,
II-103. N-[4-(2-chloro-5-pyridyl)butyl]trimethylenediamine,
II-104. N-[1-(2-chloro-5-pyridyl)propyl]trimethylenediamine, and
II-105. N-[2-methyl-1-(2-chloro-5-pyridyl)propyl]ethylenediamine.

Specific examples of the compound of general formula (III) which is likewise a starting material include 1-nitro-2,2-bis(methylthio)ethylene,
1-nitro-2,2-bis(ethylthio)ethylene,
1-nitro-2,2-bis(benzylthio)ethylene, and
2-nitromethylene-1,3-dithiolane.

The above process is specifically described by the following illustrative example:

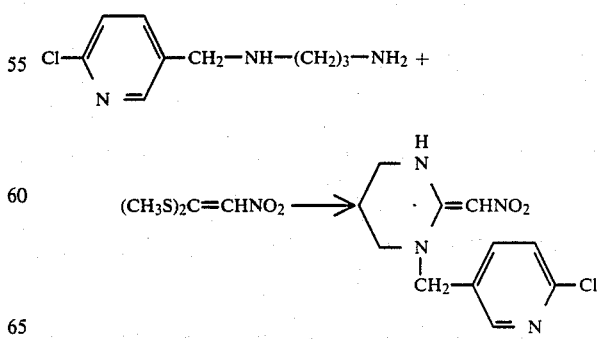

Desirably, the above process for producing the compound of this invention can be carried out using a solvent or a diluent. For this purpose, all inert solvents and diluents can be used.

Examples of such solvents or diluents include water; aliphatic, alicyclic and aromatic hydrocarbons (which may optionally be chlorinated) such as hexane, cyclohexane, petroleum ether, ligroin, benzene, toluene, xylene, methylene, chloride, chloroform, carbon tetrachloride, ethylene chloride, trichloroethylene and chlorobenzene; ethers such as diethyl ether, methyl ethyl ether, diisopropyl ether, dibutyl ether, propylene oxide, dioxane and tetrahydrofuran; ketones such as acetone, methyl ethyl ketone, methyl isopropyl ketone and methyl isobutyl ketone; nitriles such as acetonitrile, propionitrile and acrylonitrile; alcohols such as methanol, ethanol, isopropanol, butanol and ethylene glycol; esters such as ethyl acetate and amyl acetate; acid amides such as dimethylformamide and dimethylacetamide; sulfones and sulfoxides such as dimethyl sulfoxide and sulfolane; and bases such as pyridine.

The above process can be carried out over a wide temperature range. Generally, it can be carried out at a temperature between about $-20°$ C. and the boiling point of the mixture, preferably between about $0°$ C. and about $100°$ C. Desirably, the reaction is carried out under normal atomospheric pressure, but it is also possible to operate under elevated or reduced pressures.

The compounds of general formula (I) in accordance with this invention may also be produced by an alternative process schematically shown below.

Alternative process 1

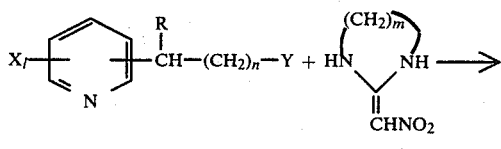

(IV)        (VI)

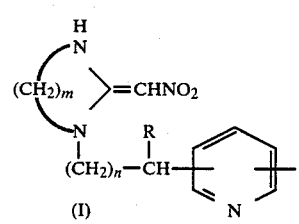

(I)

(In the above formulae, R, X, l, m, n and Y are as defined hereinabove.)

The compounds of general formula (II) in accordance with this invention can be produced for example, by the following process (ii):

Process (ii)

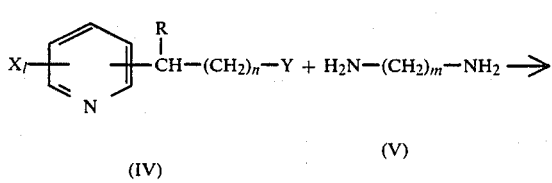

(IV)        (V)

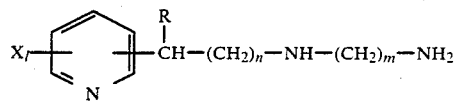

(II)

(In the formulae, R, X, l, m, n and Y are as defined hereinabove.)

In the above reaction scheme, R, X, l, m and n may be the same as those given above for the process (i). Y represents halogen atom such as fluoro, chloro, bromo and iodo, or the group $-OSO_2R''$, in which $R''$ represents the same lower alkyl as exemplified above for the process (i), or aryl groups such as phenyl and p-tolyl.

In the process for producing the compounds of general formula (II) of this invention represented by the reaction scheme, specific examples of the starting compound of general formula (IV) include IV-1. 5-methyl-2-pyridylmethyl chloride,
IV-2. 6-methyl-2-pyridylmethyl chloride,
IV-3. 4-methyl-2-pyridylmethyl chloride,
IV-4. 5-ethyl-2-pyridylmethyl chloride,
IV-5. 5-butyl-2-pyridylmethyl chloride,
IV-6. 4,6-dimethyl-2-pyridylmethyl chloride,
IV-7. 3-chloro-2-pyridylmethyl chloride,
IV-8. 5-chloro-2-pyridylmethyl chloride,
IV-9. 3,5-dichloro-2-pyridylmethyl chloride,
IV-10. 5-fluoro-2-pyridylmethyl chloride,
IV-11. 6-bromo-2-pyridylmethyl chloride,
IV-12. 2-(5-ethyl-2-pyridyl)ethyl chloride,
IV-13. 6-chloro-4-methyl-2-pyridylmethyl chloride,
IV-14. 5-methyl-3-pyridylmethyl chloride,
IV-15. 2-methyl-5-pyridylmethyl chloride,
IV-16. 2-phenyl-5-pyridylmethyl chloride,
IV-17. 2-benzyl-5-pyridylmethyl chloride,
IV-18. 2-chloro-3-pyridylmethyl chloride,
IV-19. 5-chloro-3-pyridylmethyl chloride,
IV-20. 5-bromo-3-pyridylmethyl chloride,
IV-21. 2-bromo-5-pyridylmethyl chloride,
IV-22. 5-fluoro-3-pyridylmethyl chloride,
IV-23. 2-fluoro-5-pyridylmethyl chloride,
IV-24. 1-(2-fluoro-5-pyridyl)ethyl chloride,
IV-25. 2-methyl-1-(2-fluoro-5-pyridyl)propyl chloride,
IV-26. 2-(2-fluoro-5-pyridyl)ethyl chloride,
IV-27. 3-(2-bromo-5-pyridyl)propyl chloride,
IV-28. 2-bromo-5-pyridylmethyl chloride,
IV-29. 4-(2-bromo-5-pyridyl)butyl chloride,
IV-30. 2-chloro-6-methyl-3-pyridylmethyl chloride,
IV-31. 2,4-dichloro-5-pyridylmethyl chloride,
IV-32. 2,6-dichloro-5-pyridylmethyl chloride,
IV-33. 2,4-dibromo-5-pyridylmethyl chloride,
IV-34. 2,4-difluoro-5-pyridylmethyl chloride,
IV-35. 2,4,5,6-tetrafluoro-3-pyridylmethyl chloride,
IV-36. 2,4,5,6-tetrachloro-3-pyridylmethyl chloride,
IV-37. 2-methoxy-3-pyridylmethyl chloride,
IV-38. 2-methoxy-5-pyridylmethyl chloride,
IV-39. 2-ethoxy-5-pyridylmethyl chloride,
IV-40. 2-isopropoxy-5-pyridylmethyl chloride,
IV-41. 2-phenoxy-5-pyridylmethyl chloride,
IV-42. 2-(2,4-dichlorophenoxy)-5-pyridylmethyl chloride,
IV-43. 2-methylthio-3-pyridylmethyl chloride,
IV-44. 2-methylthio-5-pyridylmethyl chloride,
IV-45. 4-methyl-2-methylthio-5-pyridylmethyl chloride, IV-46. 2-phenylthio-5-pyridylmethyl chloride
IV-47. 2-(4-chlorophenylthio)-5-pyridylmethyl chloride,
IV-48. 2-ethylthio-5-pyridylmethyl chloride,
IV-49. 2-methylsulfinyl-5-pyridylmethyl chloride,
IV-50. 2-methylsufonyl-5-pyridylmethyl chloride,
IV-51. 4-chloro-2-fluoro-5-pyridylmethyl chloride,
IV-52. 6-chloro-2-methyl-3-pyridylmethyl chloride,
IV-53. 2-chloro-4-methyl-5-pyridylmethyl chloride,
IV-54. 2-allyl-5-pyridylmethyl chloride,
IV-55. 2-propargyl-5-pyridylmethyl chloride,
IV-56. 2,3-dichloro-5-pyridylmethyl chloride,
IV-57. 2-(1-propenyl)-5-pyridylmethyl chloride,
IV-58. 2-chloro-4-pyridylmethyl chloride,
IV-59. 2-fluoro-4-pyridylmethyl chloride,
IV-60. 2,6-dichloro-4-pyridylmethyl chloride,
IV-61. 2,6-difluoro-4-pyridylmethyl chloride,
IV-62. 2-methyl-4-pyridylmethyl chloride,
IV-63. 1-(2-chloro-4-pyridyl)ethyl chloride,
IV-64. 2-chloro-6-methyl-4-pyridylmethyl chloride,
IV-65. 2,6-dimethyl-4-pyridylmethyl chloride,
IV-66. 2-bromo-4-pyridylmethyl chloride,
IV-67. 2,6-dibromo-4-pyridylmethyl chloride,
IV-68. 2,3,5,6-tetrafluoro-4-pyridylmethyl chloride,
IV-69. 3-chloro-2-fluoro-5-pyridylmethyl chloride,
IV-70. 3-bromo-2-fluoro-5-pyridylmethyl chloride,
IV-71. 2-chloro-3-fluoro-5-pyridylmethyl chloride,
IV-72. 2,3,4-trichloro-5-pyridylmethyl chloride,
IV-73. 3-chloro-2-methylthio-5-pyridylmethyl chloride
IV-74. 2-chloro-5-pyridylmethyl chloride,
IV-75. 2-(2-chloro-5-pyridyl)ethyl chloride,
IV-76. 1-(2-chloro-5-pyridyl)ethyl chloride, and
IV-77. 3-(2-chloro-5-pyridyl)propyl chloride.

The corresponding bromides and p-toluenesulfonates can also be cited instead of the above chlorides.

Specific examples of the compound of general formula (V) which is likewise a starting material include ethylenediamine,
trimethylenediamine, and
tetramethylenediamine.

The above process is specifically described by the following illustrative example:

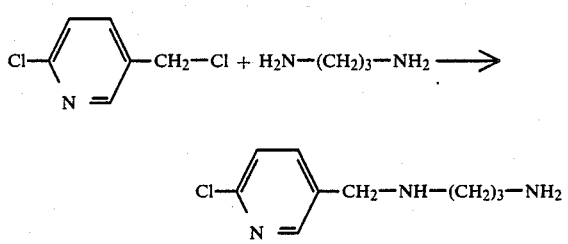

The above process can be carried out by using the same inert solvents or diluents as exemplified for the process (i).

The above reaction may be carried out in the presence of an acid binder. Examples of the acid binder are the hydroxides, carbonates, bicarbonates and alcoholates of alkali metals, and tertiary amines such as triethylamine, diethylaniline and pyridine, which are generally used.

As is the case with the process (i), the above process can be carried out over a wide temperature range. The reaction is carried out desirably under normal atmospheric pressure, but it is also possible to operate under elevated or reduced pressure.

The compounds of general formula (II), provided that n represents O, may also be produced by a process schematically shown below as an alternative process in addition to the above process (ii).

Alternative process 2

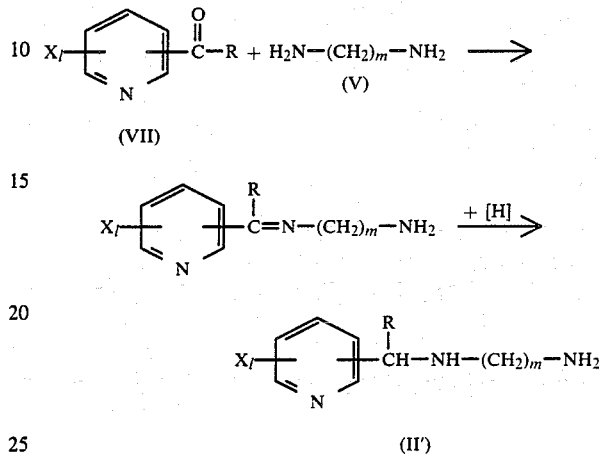

(In the formulae, X, R, l, and m are as defined hereinabove.)

As shown by the above reaction scheme, the compound of general formula (II') can be produced by reacting a reducing agent such as sodium borohydride ($NaBH_4$) or the like with the imine which is produced by reacting the pyridine aldehyde derivative or the pyridylalkylketone derivative of general formula (VII) with the compound of general formula (V). Moreover, the compounds of general formula (II), provided that R represents a hydrogen atom and n represents O, may also be produced by a process schematically shown below as an alternative process.

Alternative process 3

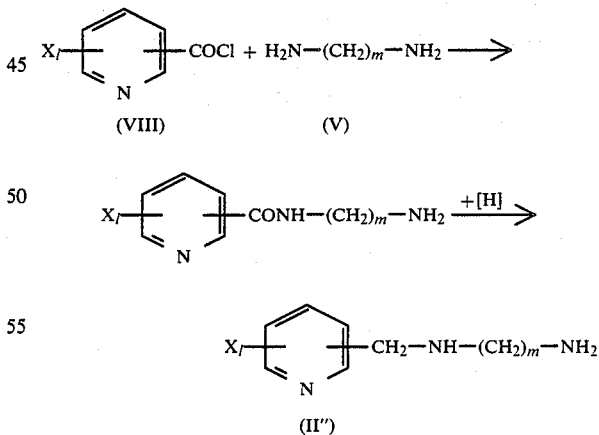

(In the formulae, X, l, and m are as defined hereinabove.)

As shown by the above reaction scheme, the compounds of general formula (II') can be produced by reacting a reducing agent such as lithium aluminum hydride ($LiAlH_4$) or the like with the nicotinic amide derivative or the picolinic amide derivative which is produced by reacting the pyridylcarbonyl chloride derivative of general formula (VIII) with the compound of general formula (V).

The compound of general formula (II), provided that R represents a hydrogen atom, n represents 0 and m represents 3, may also be produced by a process schematically shown below as an alternative process.

Alternative process 4

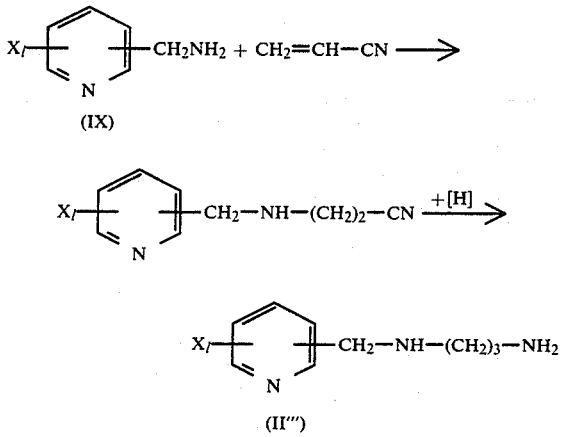

(In the formulae, X and l, are as defined hereinabove.)

As shown by the above reaction scheme, the compounds of general formula (II''') can be produced by reducing, in accordance with the same as aforesaid alternative process 2, the adducts which are produced by reacting acrylonitrile with the compounds of general formula (IX). For example, N-(2-chloro-5-pyridylmethyl)trimethylenediamine which is compound No. II-97 mentioned later can also be produced by the above alternative process 4.

The compounds of general formula (II), provided that m represents 2, may also be produced by a process schematically shown below as an alternative process.

Alternative process 5

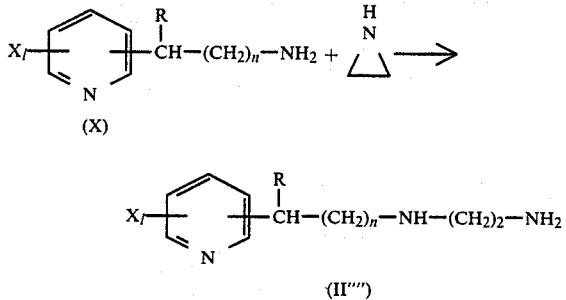

(In the formulae, R, X, l and n are as defined hereinabove.)

As shown by the above reaction scheme, the compounds of general formula (II'''') can also be produced by reacting the pyridylalkylamine derivatives of general formula (X) with ethyleneimine.

The compounds of this invention may be present in the form of salts. The salts may, for example, be inorganic salts, sulfonates, organic acid salts, and metal salts. Specific examples of the compounds of this invention in the form of salts include 1-(2-chloro-5-pyridylmethyl)-2-(nitromethylene)tetrahydropyrimidine hydrochloride,
1-(2-chloro-5-pyridylmethyl)-2-(nitromethylene)tetrahydropyrimidine p-toluenesulfonate,
1-(2-chloro-5-pyridylmethyl)-2-(nitromethylene)imidazolidine hydrochloride,
1-(2-chloro-5-pyridylmethyl)-2-(nitromethylene)imidazolidine cupric acetate,
1-(2-bromo-5-pyridylmethyl)-2-(nitromethylene)tetrahydropyrimidine hydrochloride,
1-(2-methoxy-5-pyridylmethyl)-2-(nitromethylene)imidazolidine hydrochloride,
1-(2-fluoro-5-pyridylmethyl)-2-(nitromethylene)imidazolidine p-toluenesulfonate,
1-(2-bromo-5-pyridylmethyl)-2-(nitromethylene)tetrahydropyrimidine cupric acetate, and
1-(3-bromo-5-pyridylmethyl)-2-(nitromethylene)imidazolidine succinate.

As insecticides, the compounds of this invention may be used directly upon dilution with water, or in various formulations obtained by methods generally practiced in the production of agricultural chemicals using agriculturally acceptable adjuvants. In actual use, these various formulations may be applied directly or after diluting them with water to the desired concentrations.

The agriculturally acceptable adjuvants as referred to herin include, for example, diluents (solvents, extenders, carriers), surface-active agents (solubilizing agents), emulsifiers, dispersing agents, wetting agents, stabilizers, stickers, aerosol propellants and synergists.

Examples of the solvents are water, and organic solvents, for example hydrocarbons [such as n-hexane, petroleum ether, petroleum fractions (e.g. paraffin waxes, kerosene, light oils, middle oils, and heavy oils), benzene, toluene, and xylene], halogenated hydrocarbons (such as methylene chloride, carbon tetrachloride, ethylene chloride, ethylene dibromide, chlorobenzene and chloroform), alcohols (such as methanol, ethanol, propanol and ethylene glycol), ethers (such as diethyl ether, ethylene oxide and dioxane), alcohol ethers (such as ethylene glycol monomethyl ether), ketones (such as acetone and isophorone), esters (such as ethyl acetate and amyl acetate), amides (such as dimethylformamide and dimethylacetamide) and sulfoxides (such as dimethyl sulfoxide).

Examples of the extenders or carriers include inorganic powders, for example slaked lime, magnesium lime, gypsum, calcium carbonate, silica, perlite, pumice, calcite, diatomaceous earth, amorphous silica, alumina, zeolites, and clay minerals (such as pyrophyllite, talc, montmorillonite, beidellite, vermiculite, kaolinite and mica); vegetable powders such as cereal powders, starches, processed starches, sugar, glucose and crushed stalks of plants; and powders of synthetic resins such as phenolic resins, urea resins, and vinyl chloride resins.

Examples of the surface-active agents include anionic surface-active agents such as alkylsulfonic acid esters (such as sodium laurylsulfate), arylsulfonic acids (such as alkylarylsulfonic acid salts and sodium alkylnaphthalenesulfonates), succinic acid salts, and salts of sulfuric acid esters of polyethylene glycol alkylaryl ethers; cationic surface-active agents such as alkylamines (e.g., laurylamine, stearyl trimethyl ammonium chloride and alkyl dimethylbenzyl ammonium chlorides) and polyoxyethylene alkylamines; nonionic surface-active agents such as polyoxyethylene glycol ethers (e.g., polyoxyethylene alkylaryl ethers and the condensation products thereof), polyoxyethylene glycol esters (e.g., polyoxyethylene fatty acids esters), and polyhydric alcohol esters (e.g., polyoxyethylene sorbitan monolaurate); and amphoteric surface-active agents.

Examples of other adjuvants include stabilizers; stickers (such as agricultural soaps, casein lime, sodium alginate, polyvinyl alcohol, vinyl acetate-type adhesives and acrylic adhesives); aerosol propellants (such as trichlorofluoromethane, dichlorofluoromethane, 1,2,2-trichloro-1,1,2-trifluoroethane, chlorobenzene, LNG, and lower ethers); combustion controlling agents for fumigants (such as nitrites, zinc powder and dicyandiamide); oxygen-yielding agents (such as chlorates); effect-prolonging agents; dispersion stabilizers [such as casein, tragacanth, carboxymethyl cellulose (CMC), and polyvinyl alcohol (PVA)]; and synergists.

The compounds of this invention can be formulated into various forms by methods generally practiced in the production of agricultural chemicals. Illustrative of such forms are emulsifiable concentrates, oil preparations, wettable powders, soluble powders, suspensions, dusts, granules, pulverulent preparations, fumigants, tablets, aerosols, pastes and capsules.

The insecticides of this invention may contain about 0.1 to about 95% by weight, preferably about 0.5 to about 90% by weight, of the aforesaid active ingredient.

In actual use, the suitable amount of the active compound in the aforesaid various formulations and ready-to-use preparations is generally about 0.0001 to about 20% by weight, preferably about 0.005 to about 10% by weight.

The content of the active ingredient can be properly varied depending upon the type of the formulation, the method, purpose, time and locus of its application, and the state of occurence of noxious insects.

If required, the compounds of this invention may be used in combination with other agricultural chemicals, for example other insecticides, fungicides, other miticides, other nematocides, antiviral agents, herbicides, plant growth regulators and attractants (such as organophosphate compounds, carbamate compounds, dithio (or thiol) carbamate compounds, organochlorine compounds, dinitro compounds, organosulfur or organometallic compounds, antibiotics, substituted diphenyl ether compounds, urea compounds, and triazine compounds), and/or fertilizers.

Various formulations and ready-to-use preparations containing the aforesaid active ingredient of the invention can be applied by various methods generally practiced in the field of agricultural chemical application, for example spraying (liquid spraying, misting, atomizing, dusting, granule scattering, water surface application, pouring, etc.); fumigation; soil application (mixing, sprinkling, vaporing, pouring, etc.); surface application (coating, banding, powder coating, covering, etc.); dipping; and baiting. It can also be used by the so-called ultralow volume spraying method. According to this method, the active ingredient may be included in an amount of 100%.

The rate of application per unit area is, for example, about 0.03 to about 10 Kg, preferably about 0.3 to about 6 Kg, per hectare. In special cases, however, it may, and sometimes should, be outside the specified range.

According to this invention, there can be provided an insecticidal composition comprising the compound of general formula (I) as an active ingredient and a diluent (a solvent and/or an extender and/or a carrier) and/or a surface-active agent, and if further required, a stabilizer, a sticker, a synergist, etc.

This invention also provides a method for controlling noxious insects, which comprises applying to a noxious insect and/or its habitat or the locus of its occurrence the compound of general formula (I) alone or in admixture with a diluent (a solvent and/or an extender and/or a carrier) and/or a surface-active agent and if further required, a stabilizer, a sticker, a synergist, etc.

The following examples illustrate the present invention specifically. It should be noted however that the invention is not limited to these specific examples alone.

EXAMPLE 1

2-chloro-5-pyridylmethyl chloride (16.2 g) in a solution of acetonitrile (30 ml) was added dropwise to a solution of ethylenediamine (18 g) in acetonitrile (100 ml) at room temperature during 1 hour.

The reaction mixture was stirred at room temperature for an hour and next at 40° C. for 2 hours.

After the stirring, acetonitrile was evaporated under reduce pressure. Ether was added to the residue and insoluble salts were filtrated off, and then ether and excess ethylenediamine were evaporated under reduced pressure to give N-(2-chloro-5-pyridylmethyl)ethylenediamine (16 g) of the following formula as colorless oil. $n_D^{20} 1.5627$.

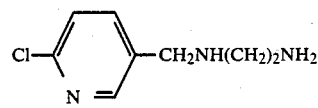

(Compound No. II-95)

EXAMPLE 2

2-bromo-5-pyridylmethyl bromide (25 g) in a solution of acentonitrile was added dropwise to a solution of ethylenediamine (30 g) in acetonitrile (80 ml) at 0° C. After the reaction was stirred at room temperature for some time, the produced insoluble salts were filtrated off and then the filtrate was concentrated on a water bath at 40° C. to give N-(2-bromo-5-pyridylmethyl)ethylenediamine (22 g).
$n_D^{26} 1.5586$.

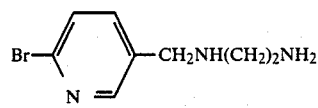

(Compound No. II-30)

EXAMPLE 3

6-methylpicolinic aldehyde (12.1 g) was added to a solution of ethylenediamine (24 g) in anhydrous dioxane (200 ml). The mixture was stirred at room temperature for 3 hours. After the stirring, the mixture was heated and the mixture (120 ml) of the dioxane and the produced water was distilled off to complete the Schiff's base reaction. The contents were cooled at room temperature and sodium borohydride (7.6 g) was added to the contents incrementally. After the adding, the mixture was stirred at room temperature for 8 hours. After the volatile matter was distilled in vacuum from the mixture, ice water was added to the residue and the product was extracted with chloroform. The extract was evaporated to give N-(2-methyl-6-pyridylmethyl)ethylenediamine (8.3 g).

b.p. 127°–129° C./0.1 mmHg.

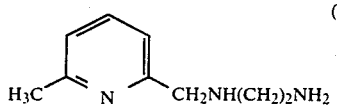

(Compound No. II-19)

EXAMPLE 4

2-Ethoxy-5-pyridylmethyl chloride hydrochloride (9.6 g) in an aqueous solution was added dropwise to the mixed solution of trimethylenediamine (11.1 g) and 20% aqueous solution (22 g) of sodium hydroxide at 0°–5° C. After the reaction mixture was stirred at room temperature for some time, water and excess trimethylenediamine were distilled off under reduced pressure from the contents and after the inorganic salts were filtered off, the produced viscous and oily substance was evaporated in vacuum to give N-(2-ethoxy-5-pyridylmethyl)-trimethylenediamine (6.3 g).

b.p. 134°–135° C./0.08 mmHg.

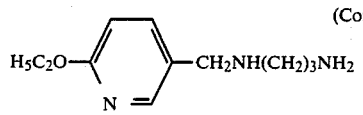

(Compound No. II-52)

EXAMPLE 5

Table 1 below shows the compounds of general formula (II) which were synthesized the same way as in Example 1, 2 or 4.

TABLE 1

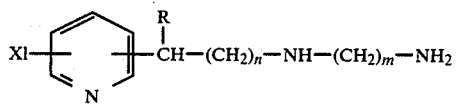

| Compound No. | m | n | R | Pyridine-bonded position | Xl | physical constant |
|---|---|---|---|---|---|---|
| II-1 | 2 | 0 | H | 2-position | 5-$CH_3$ | $n_D^{20}$ 1.5397 |
| II-2 | 3 | 0 | H | 2-position | 5-$CH_3$ | $n_D^{20}$ 1.5348 |
| II-20 | 3 | 0 | H | 5-position | 2-$CH_3$ | b. p. 134~135° C./0.1 mmHg |
| II-24 | 2 | 0 | H | 3-position | 2-Cl | $n_D^{25}$ 1.5575 |
| II-31 | 3 | 0 | H | 5-position | 2-Br | $n_D^{26}$ 1.5581 |
| II-33 | 2 | 0 | H | 5-position | 2-F | b. p. 118~120° C./0.1 mmHg |
| II-34 | 3 | 0 | H | 5-position | 2-F | b. p. 120~122° C./0.1 mmHg |
| II-51 | 2 | 0 | H | 5-position | 2-$OCH_3$ | b. p. 142~144° C./0.1 mmHg |
| II-54 | 2 | 0 | H | 5-position | 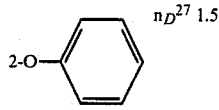 | $n_D^{27}$ 1.5845 |
| II-55 | 3 | 0 | H | 5-position | 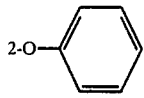 | $n_D^{27}$ 1.5775 |
| II-58 | 2 | 0 | H | 5-position | 2-$SCH_3$ | b. p. 130~131° C./0.07 mmHg |
| II-59 | 3 | 0 | H | 5-position | 2-$SCH_3$ | b. p. 143~145° C./0.1 mmHg |
| II-97 | 3 | 0 | H | 5-position | 2-Cl | $n_D^{22}$ 1.5562 |

EXAMPLE 6

Table 2 below shows the compounds of general formula (II) which were further synthesized the same way as in the above Example 1, 2 or 4 for the purpose of supplying the starting materials for the synthesis of the compounds of general formula (I).

TABLE 2

| Compound No. | Compounds (products) |
|---|---|
| II-3. | N—(6-methyl-2-pyridylmethyl)ethylenediamine |
| II-4. | N—(6-methyl-2-pyridylmethyl)trimethylenediamine |
| II-5. | N—(4-methyl-2-pyridylmethyl)ethylenediamine |
| II-6. | N—(4-methyl-2-pyridylmethyl)trimethylenediamine |
| II-7. | N—(5-ethyl-2-pyridylmethyl)ethylenediamine |
| II-8. | N—(5-buthyl-2-pyridylmethyl)ethylenediamine |
| II-9. | N—(4,6-dimethyl-2-pyridylmethyl)ethylenediamine |
| II-10. | N—(3-chloro-2-pyridylmethyl)ethylenediamine |
| II-11. | N—(5-chloro-2-pyridylmethyl)ethylenediamine |
| II-12. | N—(5-chloro-2-pyridylmethyl)trimethylenediamine |
| II-13. | N—(3,5-dichloro-2-pyridylmethyl)ethylenediamine |
| II-14. | N—(5-fluoro-2-pyridylmethyl)trimethylenediamine |
| II-15. | N—(6-bromo-2-pyridylmethyl)ethylenediamine |
| II-16. | N—[2-(5-ethyl-2-pyridyl)ethyl]trimethylenediamine |
| II-17. | N—(6-chloro-4-methyl-2-pyridylmethyl)ethylenediamine |
| II-18. | N—(5-methyl-3-pyridylmethyl)ethylenediamine |
| II-21. | N—(2-phenyl-5-pyridylmethyl)ethylenediamine |
| II-22. | N—(2-phenyl-5-pyridylmethyl)trimethylenediamine |
| II-23. | N—(2-benzyl-5-pyridylmethyl)ethylenediamine |
| II-25. | N—(2-chloro-5-pyridylmethyl)trimethylenediamine |
| II-26. | N—(5-chloro-3-pyridylmethyl)ethylenediamine |
| II-27. | N—(5-chloro-3-pyridylmethyl)trimethylenediamine |
| II-28. | N—(5-bromo-3-pyridylmethyl)ethylenediamine |
| II-29. | N—(5-bromo-3-pyridylmethyl)trimethylenediamine |
| II-32. | N—(5-fluoro-3-pyridylmethyl)ethylenediamine |
| II-35. | N—[1-(2-fluoro-5-pyridyl)ethyl]ethylenediamine |
| II-36. | N—[2-methyl-1-(2-fluoro-5-pyridyl)propyl]ethylenediamine |
| II-37. | N—[2-(2-fluoro-5-pyridyl)ethyl]ethylenediamine |
| II-38. | N—[3-(2-bromo-5-pyridyl)propyl]trimethylenediamine |
| II-39. | N—(2-bromo-5-pyridylmethyl)tetramethylenediamine |
| II-40. | N—[4-(2-bromo-5-pyridyl)butyl]trimethylenediamine |
| II-41. | N—(2-chloro-6-methyl-3-pyridylmethyl)ethylenediamine |
| II-42. | N—(2,4-dichloro-5-pyridylmethyl)trimethylenediamine |
| II-43. | N—(2,6-dichloro-3-pyridylmethyl)ethylenediamine |
| II-44. | N—(2,4-dibromo-5-pyridylmethyl)ethylenediamine |
| II-45. | N—(2,4-difluoro-5-pyridylmethyl)ethylenediamine |

TABLE 2-continued

| Compound No. | Compounds (products) |
|---|---|
| II-46. | N—(2,4,5,6-tetrafluoro-3-pyridylmethyl)ethylenediamine |
| II-47. | N—(2,4,5,6-tetrachloro-3-pyridylmethyl)ethylenediamine |
| II-48. | N—(2-methoxy-3-pyridylmethyl)trimethylenediamine |
| II-49. | N—(2-methoxy-5-pyridylmethyl)ethylenediamine |
| II-50. | N—(2-methoxy-5-pyridylmethyl)trimethylenediamine |
| II-53. | N—(2-isopropoxy-5-pyridylmethyl)ethylenediamine |
| II-56. | N—[2-(2,4-dichlorophenoxy)-5-pyridylmethyl]ethylenediamine |
| II-57. | N—(2-methylthio-3-pyridylmethyl)ethylenediamine |
| II-60. | N—(4-methyl-2-methylthio-5-pyridylmethyl)ethylenediamine |
| II-61. | N—(2-phenylthio-5-pyridylmethyl)ethylenediamine |
| II-62. | N—[2-(4-chlorophenylthio)-5-pyridylmethyl]ethylenediamine |
| II-63. | N—(2-ethylthio-5-pyridylmethyl)ethylenediamine |
| II-64. | N—(2-methylsulfinyl-5-pyridylmethyl)ethylenediamine |
| II-65. | N—(2-methylsulfonyl-5-pyridylmethyl)trimethylenediamine |
| II-66. | N—(4-chloro-2-fluoro-5-pyridylmethyl)trimethylenediamine |
| II-67. | N—(6-chloro-2-methyl-3-pyridylmethyl)ethylenediamine |
| II-68. | N—(2-chloro-4-methyl-5-pyridylmethyl)ethylenediamine |
| II-69. | N—(allyl-5-pyridylmethyl)ethylenediamine |
| II-70. | N—(2-propargyl-5-pyridylmethyl)ethylenediamine |
| II-71. | N—(2,3-dichloro-5-pyridylmethyl)ethylenediamine |
| II-72. | N—[2-(1-propenyl)-5-pyridylmethyl]ethylenediamine |
| II-73. | N—(2-chloro-4-pyridylmethyl)ethylenediamine |
| II-74. | N—(2-chloro-4-pyridylmethyl)trimethylenediamine |
| II-75. | N—(2-fluoro-4-pyridylmethyl)ethylenediamine |
| II-76. | N—(2-fluoro-4-pyridylmethyl)trimethylenediamine |
| II-77. | N—(2,6-dichloro-4-pyridylmethyl)ethylenediamine |
| II-78. | N—(2,6-difluoro-4-pyridylmethyl)trimethylenediamine |
| II-79. | N—(2-methyl-4-pyridylmethyl)ethylenediamine |
| II-80. | N—(2-methyl-4-pyridylmethyl)trimethylenediamine |
| II-81. | N—[1-(2-chloro-4-pyridyl)ethyl]ethylenediamine |
| II-82. | N—(2-chloro-6-methyl-4-pyridylmethyl)ethylenediamine |
| II-83. | N—(2-chloro-6-methyl-4-pyridylmethyl)trimethylenediamine |
| II-84. | N—(2,6-dimethyl-4-pyridylmethyl)ethylenediamine |
| II-85. | N—(2-bromo-4-pyridylmethyl)ethylenediamine |
| II-86. | N—(2,6-dibromo-4-pyridylmethyl)ethylenediamine |
| II-87. | N—(2,3,5,6-tetrafluoro-4-pyridylmethyl)ethylenediamine |
| II-88. | N—(2,3,5,6-tetrafluoro-4-pyridyl)trimethylenediamine |
| II-89. | N—(2,6-dichloro-4-pyridylmethyl)trimethylenediamine |
| II-90. | N—(3-chloro-2-fluoro-5-pyridylmethyl)ethylenediamine |
| II-91. | N—(3-bromo-2-fluoro-5-pyridylmethyl)ethylenediamine |
| II-92. | N—(2-chloro-3-fluoro-5-pyridylmethyl)ethylenediamine |
| II-93. | N—(2,3,4-trichloro-5-pyridylmethyl)ethylenediamine |
| II-94. | N—(3-chloro-2-methylthio-5-pyridylmethyl)ethylenediamine |
| II-96. | N—[2-(2-chloro-5-pyridyl)ethyl]ethylenediamine |
| II-98. | N—[2-(2-chloro-5-pyridyl)ethyl]trimethylenediamine |
| II-99. | N—[1-(2-chloro-5-pyridyl)ethyl]trimethylenediamine |
| II-100. | N—[3-(2-chloro-5-pyridyl)propyl]trimethylenediamine |
| II-101. | N—[1-(2-chloro-5-pyridyl)ethyl]ethylenediamine |
| II-102. | N—(2-chloro-5-pyridylmethyl)tetramethylenediamine |
| II-103. | N—[4-(2-chloro-5-pyridyl)butyl]trimethylenediamine |
| II-104. | N—[1-(2-chloro-5-pyridyl)propyl]trimethylenediamine |
| II-105. | N—[2-methyl-1-(2-chloro-5-pyridyl)propyl]ethylenediamine |

The referential examples below illustrate synthesis of the compounds of general formula (IV) which are the intermediates for the aforesaid compounds of general formula (II) and part of which is new.

REFERENTIAL EXAMPLE 1a

15% methylmercaptan sodium salt (77 g) was added to 6-chloronicotinic acid (15.8 g) dissolved in 20% aqueous solution of sodium hydroxide (22 g). The reaction mixture was stirred at 70°~80° C. for 10 hours. After the cooling, the precipitate produced by neutralization was collected by filtration and recrystallized from chloroform to give 6-methylthionicotinic acid (15.3 g).

m.p. 186°~188° C.

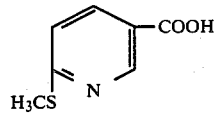

REFERENTIAL EXAMPLE 1b

Thionylchloride (23.8 g) was added to 6-methylthionicotinic acid (15.3 g) (from the above referential example 1a). The reaction mixture was gradually heated with stirring and refluxed until the generation of hydrogen chloride ceased. 6-methylthionicotinoylchloride was stoichiometricly obtained by distilling off excess thionylchloride under reduced pressure. 6-methylthionicotinoylchloride dissolved in ether was added dropwise to 20% aqueous solution of sodium borohydride (6.5 g) at 0°~10° C. After adding, the mixture was stirred for one hour and the ether layer was separated and dried. The ether layer was evaporated under reduced pressure to give 2-methylthiopyridine-5-methanol (9.6 g).

$n_D^{22}$ 1.6084.

REFERENTIAL EXAMPLE 1c

Thionylchloride (7.7 g) was added to 2-methylthiopyridine-5-methanol (7.8 g) (from the above referential example 1c) in chloroform (30 ml) at room temperature. After stirring for some time, the volatile matter was distilled off under reduced pressure to give 2-methylthio-5-chloromethyl pyridine hydrochloride (10.4 g) stoichiometrically (m.p. 127°~130° C.)

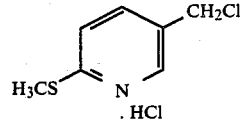

The compounds synthesized the same way as in the above referential examples 1a, 1b, 1c are exemplified below. Method of referential example 1a:

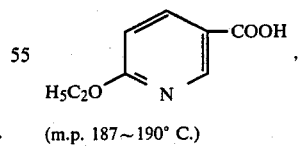

(m.p. 187~190° C.)

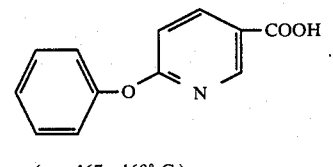

(mp. 167~168° C.)

Method of referential example 1b:

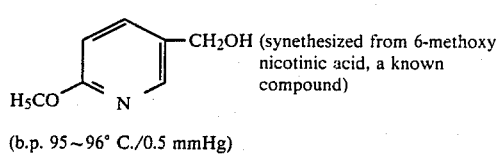 (synethesized from 6-methoxy nicotinic acid, a known compound)

(b.p. 95~96° C./0.5 mmHg)

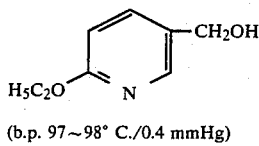

(b.p. 97~98° C./0.4 mmHg)

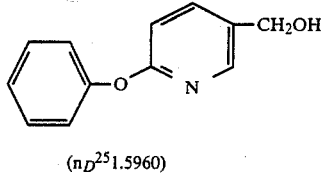

($n_D^{25}$ 1.5960)

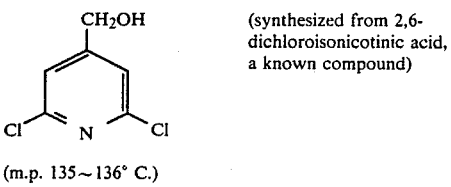 (synthesized from 2,6-dichloroisonicotinic acid, a known compound)

(m.p. 135~136° C.)

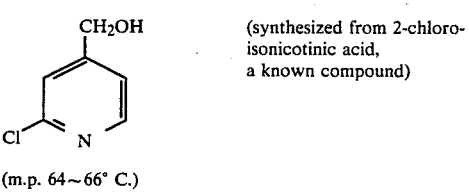 (synthesized from 2-chloro-isonicotinic acid, a known compound)

(m.p. 64~66° C.)

Method of referential example 1c:

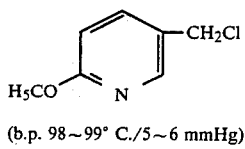

(b.p. 98~99° C./5~6 mmHg)

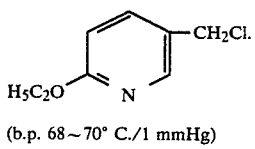

(b.p. 68~70° C./1 mmHg)

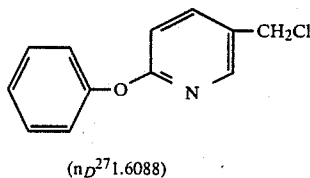

($n_D^{27}$ 1.6088)

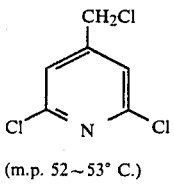

(m.p. 52~53° C.)

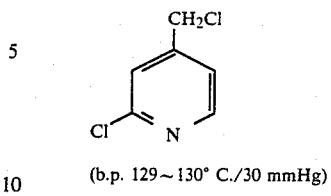

(b.p. 129~130° C./30 mmHg)

EXAMPLE 7

N-(2-chloro-5-pyridylmethyl)ethylenediamine (18.6 g), 1-nitro-2,2-bis(methylthio)ethylene (16.5 g) and methanol (100 ml) were mixed at room temperature.

The mixture was gradually heated with stirring and stirred at 50° C. until the generation of methylmercaptan ceased. After the reaction, the reaction mixture was cooled to room temperatures and the resulting crystals were collected by filtration to give 1-(2-chloro-5-pyridylmethyl)-2-(nitromethylene)-imidazolidine (19 g) of the following formula as pale yellow crystals: m.p. 165°~166° C.

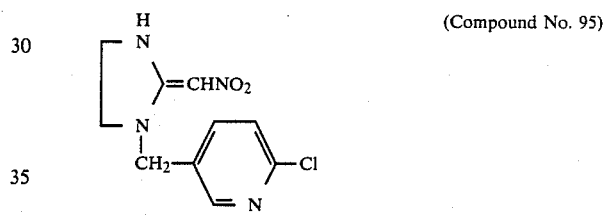

(Compound No. 95)

EXAMPLE 8

N-(2-fluoro-5-pyridylmethyl)ethylene diamine (1.7 g), 1-nitro-2,2-bis(methylthio)ethylene (1.7 g) and ethanol (10 ml) were mixed at room temperature.

The mixture was gradually heated with stirring and refluxed until the generation of methylmercaptan ceased. After cooling to room temperature, the resulting crystals were collected by filtration and dried to give light yellow crystals 1-(2-fluoro-5-pyridylmethyl)-2-(nitromethylene)imidazolidine (1.7 g).

m.p. 139°~142° C.

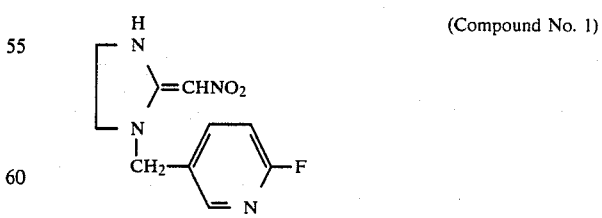

(Compound No. 1)

EXAMPLE 9

Table 3 below shows the compounds of general formula (I) which were synthesized the same way as in Example 7 and 8.

TABLE 3

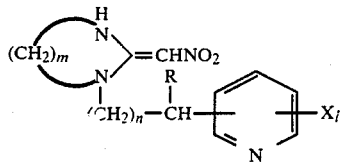

| Compound No. | m | n | R | Pyridine-bonded position | $X_l$ | m.p. |
|---|---|---|---|---|---|---|
| 2 | 2 | 0 | H | 2-position | 5-CH₃ | 130~132° C. |
| 3 | 3 | 0 | H | 2-position | 5-CH₃ | 145~146° C. |
| 4 | 2 | 0 | H | 2-position | 6-Br | 176~178° C. |
| 5 | 2 | 0 | H | 5-position | 2-OC₂H₅ | 171~173° C. |
| 6 | 3 | 0 | H | 5-position | 2-OC₂H₅ | 177~179 C. |
| 7 | 2 | 0 | H | 5-position | 2-O-phenyl | 179~180° C. |
| 8 | 3 | 0 | H | 5-position | 2-O-phenyl | 185~° C. |
| 9 | 3 | 0 | H | 5-position | 2-F | 149~151° C. |
| 10 | 2 | 0 | H | 3-position | 2-Cl | 201~204° C. |
| 11 | 2 | 0 | H | 3-position | 5-Br | 180~¾° C. |
| 12 | 3 | 0 | H | 3-position | 5-Br | 192~195° C. |
| 13 | 2 | 0 | H | 5-position | 2-Br | 167~170° C. |
| 14 | 3 | 0 | H | 5-position | 2-Br | 193~195° C. |
| 15 | 2 | 0 | H | 4-position | 2-Cl | 177~179° C. |
| 16 | 3 | 0 | H | 4-position | 2-Cl | 219~222° C. |
| 17 | 2 | 0 | H | 4-position | 2,6-Cl₂ | mp. 258~160° C. |
| 18 | 2 | 0 | H | 2-position | 6-CH₃ | mp. 191~194° C. |
| 19 | 3 | 0 | H | 2-position | 6-Ch₃ | mp. 202~204° C. |
| 20 | 2 | 0 | H | 2-position | 5-Cl | mp. 145~147° C. |
| 21 | 3 | 0 | H | 2-position | 5-Cl | mp. 161~162° C. |

TABLE 3-continued

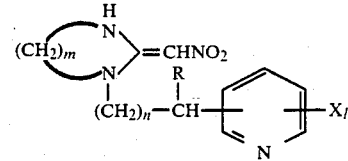

| Compound No. | m | n | R | Pyridine-bonded position | $X_l$ | m.p. |
|---|---|---|---|---|---|---|
| 22 | 2 | 0 | H | 5-position | 2-CH₃ | mp. 120~124° C. |
| 24 | 2 | 0 | H | 5-position | 2-SCH₃ | mp. 125~126° C. |
| 25 | 3 | 0 | H | 5-position | 2-SCH₃ | mp. 137~139° C. |
| 26 | 2 | 0 | H | 4-position | 2-Cl 6-CH₃ | mp. 228~230° C. |
| 29 | 2 | 0 | H | 5-position | 2-OCH₃ | mp. 159~161° C. |
| 42 | 2 | 0 | H | 5-position | 2-phenyl | mp. 196~198° C. |
| 97 | 3 | 0 | H | 5-position | 2-Cl | mp. 184~186° C. |

EXAMPLE 10

Table 4 below shows the compounds of general formula (I) which were synthesized by reacting the compounds of general formula (II) from aforesaid Examples 1, 2, 3, 4, 5 and 6 with material Nos. (III-1), (III-2), (III-3) and (III-4) shown below, the same way as in Examples 7 and 8.

Material No. (III-1): 1-nitro-2,2-bis(methylthio)ethylene
No. (III-2): 1-nitro-2,2-bis(ethylthio)ethylene
No. (III-3): 1-nitro-2,2-bis(benzylthio)ethylene
No. (III-4): 2-nitro-1,3-dithiolane

TABLE 4

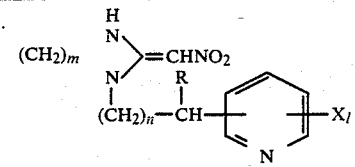

| Compound No. | material | material | Product m | n | R | Pyridine-bonded position | $X_l$ |
|---|---|---|---|---|---|---|---|
| 27 | II-84 | III-2 | 3 | 0 | H | 4-position | 2-Cl, 6-CH₃ |
| 28 | II-25 | III-1 | 3 | 0 | H | 3-position | 2-Cl |
| 30 | II-50 | III-2 | 3 | 0 | H | 5-position | 2-OCH₃ |
| 31 | II-5 | III-1 | 2 | 0 | H | 2-position | 4-CH₃ |
| 32 | II-6 | III-1 | 3 | 0 | H | 2-position | 4-CH₃ |
| 33 | II-7 | III-2 | 2 | 0 | H | 2-position | 5-C₂H₅ |
| 34 | II-8 | III-1 | 2 | 0 | H | 2-position | 5-C₄H₉—n |
| 35 | II-9 | III-1 | 2 | 0 | H | 2-position | 4,6-(CH₃)₂ |
| 37 | II-13 | III-3 | 2 | 0 | H | 2-position | 3,5-Cl₂ |
| 38 | II-14 | III-2 | 3 | 0 | H | 2-position | 5-F |
| 39 | II-16 | III-4 | 3 | 1 | H | 2-position | 5-C₂H₅ |
| 40 | II-17 | III-1 | 2 | 0 | H | 2-position | 4-CH₃, 6-Cl |
| 41 | II-18 | III-2 | 2 | 0 | H | 3-position | 5-CH₃ |

TABLE 4-continued

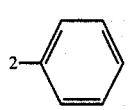

| Compound No. | material | material | m | n | R | Product Pyridine-bonded position | $X_l$ |
|---|---|---|---|---|---|---|---|
| 43 | II-22 | III-2 | 3 | 0 | H | 5-position | 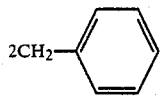 2- |
| 44 | II-23 | III-1 | 2 | 0 | H | 5-position | 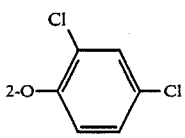 2CH$_2$- |
| 45 | II-26 | III-3 | 2 | 0 | H | 3-position | 5-Cl |
| 46 | II-27 | III-1 | 3 | 0 | H | 3-position | 5-Cl |
| 47 | II-32 | III-1 | 2 | 0 | H | 3-position | 5-F |
| 48 | II-35 | III-1 | 2 | 0 | —CH$_3$ | 5-position | 2-F |
| 49 | II-36 | III-2 | 2 | 0 | —C$_3$H$_7$—iso | 5-position | 2-F |
| 50 | II-37 | III-2 | 2 | 1 | H | 5-position | 2-F |
| 51 | II-38 | III-3 | 3 | 2 | H | 5-position | 2-Br |
| 52 | II-39 | III-1 | 4 | 0 | H | 5-position | 2-Br |
| 53 | II-40 | III-1 | 3 | 3 | H | 5-position | 2-Br |
| 54 | II-41 | III-2 | 2 | 0 | H | 3-position | 2-Cl, 6-CH$_3$ |
| 55 | II-42 | III-3 | 3 | 0 | H | 5-position | 2,4-Cl$_2$ |
| 56 | II-43 | III-1 | 2 | 0 | H | 3-position | 2,6-Cl$_2$ |
| 57 | II-44 | III-2 | 2 | 0 | H | 5-position | 2,4-Br$_2$ |
| 58 | II-45 | III-2 | 2 | 0 | H | 5-position | 2,4-F$_2$ |
| 59 | II-46 | III-3 | 2 | 0 | H | 3-position | 2,4,5,6-F$_4$ |
| 60 | II-47 | III-2 | 2 | 0 | H | 3-position | 2,4,5,6-Cl$_4$ |
| 61 | II-48 | III-1 | 3 | 0 | H | 3-position | 2-OCH$_3$ |
| 62 | II-53 | III-1 | 2 | 0 | H | 5-position | 2-C$_3$H$_7$—iso |
| 63 | II-56 | III-2 | 2 | 0 | H | 5-position | 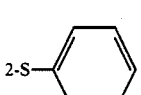 2-O- ...Cl, Cl |
| 64 | II-57 | III-2 | 2 | 0 | H | 3-position | 2-SCH$_3$ |
| 65 | II-60 | III-1 | 2 | 0 | H | 5-position | 4-CH$_3$, 2-SCH$_3$ |
| 66 | II-61 | III-1 | 2 | 0 | H | 5-position | 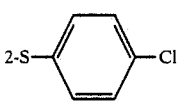 2-S- |
| 67 | II-62 | III-3 | 2 | 0 | H | 5-position |  2-S—...—Cl |
| 68 | II-63 | III-2 | 2 | 0 | H | 5-position | 2-SC$_2$H$_5$ |
| 69 | II-64 | III-2 | 2 | 0 | H | 5-position | 2-S(O)—CH$_3$ |
| 70 | II-65 | III-2 | 3 | 0 | H | 5-position |  2-S(O)$_2$—CH$_3$ |
| 71 | II-66 | III-1 | 3 | 0 | H | 5-position | 4-Cl, 2-F |
| 72 | II-67 | III-1 | 2 | 0 | H | 3-position | 6-Cl, 2-CH$_3$ |
| 73 | II-68 | III-1 | 2 | 0 | H | 5-position | 2-Cl, 4-CH$_3$ |

TABLE 4-continued

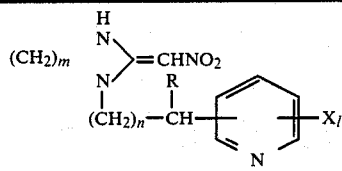

| Compound No. | material | material | m | n | R | Product Pyridine-bonded position | $X_l$ |
|---|---|---|---|---|---|---|---|
| 74 | II-69 | III-1 | 2 | 0 | H | 5-position | 2-$CH_2CH=CH_2$ |
| 75 | II-70 | III-1 | 2 | 0 | H | 5-position | 2-$CH_2C\equiv CH$ |
| 76 | II-71 | III-2 | 2 | 0 | H | 5-position | 2,3-$Cl_2$ |
| 77 | II-72 | III-2 | 2 | 0 | H | 5-position | 2-$CH=CH-CH_3$ |
| 78 | II-75 | III-4 | 2 | 0 | H | 4-position | 2-F |
| 79 | II-76 | III-4 | 3 | 0 | H | 4-position | 2-F |
| 80 | II-78 | III-1 | 3 | 0 | H | 4-position | 2,6-$F_2$ |
| 81 | II-79 | III-1 | 2 | 0 | H | 4-position | 2-$CH_3$ |
| 82 | II-80 | III-1 | 3 | 0 | H | 4-position | 2-$CH_3$ |
| 83 | II-81 | III-2 | 2 | 0 | —$CH_3$ | 4-position | 2-Cl |
| 84 | II-84 | III-2 | 2 | 0 | H | 4-position | 2,6-$(CH_3)_2$ |
| 85 | II-85 | III-2 | 2 | 0 | H | 4-position | 2-Br |
| 86 | II-86 | III-1 | 2 | 0 | H | 4-position | 2,6-$Br_2$ |
| 87 | II-87 | III-1 | 2 | 0 | H | 4-position | 2,3,5,6-$F_4$ |
| 88 | II-88 | III-1 | 3 | 0 | H | 4-position | 2,3,5,6-$F_4$ |
| 89 | II-89 | III-2 | 3 | 0 | H | 4-position | 2,6-$Cl_2$ |
| 90 | II-90 | III-1 | 2 | 0 | H | 5-position | 2-F, 3-Cl |
| 91 | II-91 | III-1 | 2 | 0 | H | 5-position | 2-F, 3-Br |
| 92 | II-92 | III-1 | 2 | 0 | H | 5-position | 2-Cl, 3-F |
| 93 | II-93 | III-1 | 2 | 0 | H | 5-position | 2,3,4-$Cl_3$ |
| 94 | II-94 | III-1 | 2 | 0 | H | 5-position | 2-$SCH_3$, 3-Cl |
| 96 | II-96 | III-1 | 2 | 1 | H | 5-position | 2-Cl |
| 98 | II-98 | III-2 | 3 | 1 | H | 5-position | 2-Cl |
| 99 | II-99 | III-1 | 3 | 0 | —$CH_3$ | 5-position | 2-Cl |
| 100 | II-100 | III-1 | 3 | 2 | H | 5-position | 2-Cl |
| 101 | II-101 | III-1 | 2 | 0 | —$CH_3$ | 5-position | 2-Cl |
| 102 | II-102 | III-1 | 4 | 0 | H | 5-position | 2-Cl |
| 103 | II-103 | III-1 | 3 | 3 | H | 5-position | 2-Cl |
| 104 | II-104 | III-2 | 3 | 0 | —$C_2H_5$ | 5-position | 2-Cl |
| 105 | II-105 | III-1 | 2 | 0 | —$C_3H_7$—iso | 5-position | 2-Cl |

EXAMPLE 11

(wettable powder)

Fifteen parts of compound No. 95 of the invention, 80 parts of a 1:5 mixture of powdery diatomaceous earth and powdery clay, 2 parts of sodium alkylbenzenesulfonate, and 3 parts of a sodium alkylnaphthalenesulfonate/formaldehyde condensate are pulverized and mixed to form a wettable powder. It is diluted with water and sprayed onto a noxious insect and/or its habitat or the locus or its occurrence.

EXAMPLE 12

(emulsifiable concentrate)

Thirty parts of compound No. 13 of the invention, 55 parts of exylene, 8 parts of polyoxyethylene alkyl phenyl ether and 7 parts of calcium alkylbenzenesulfonate are mixed with stirring to form an emulsifiable concentrate. It is diluted with water and sprayed onto a noxious insect and/or its habitat or the locus of its occurrence.

EXAMPLE 13

(dust)

Two parts of compound No. 5 of the invention and 98 parts of powdery clay are pulverized and mixed to form a dust. It is scattered over a noxious insect and/or its habitat or the locus of its occurrence.

EXAMPLE 14

(granules)

Water (25 parts) is added to a mixture consisting of 10 parts of compound No. 14 of the invention, 30 parts of bentonite (montmorillonite), 58 parts of talc and 2 parts of a lignosulfonate, and they are well kneaded. The mixture is processed by an extrusion-type granulating machine to form granules having a size of 10 to 40 mesh which are then dried at 40° to 50° C. to form granules. The granules are scattered over a noxious insect and/or its habitat or the locus of its occurrence.

EXAMPLE 15

(granules)

Ninety-five parts of clay mineral particles having a particle size distribution between 0.2 and 2 mm are put in a rotary mixer, and with rotation, 5 parts of compound No. 51 of the invention is sprayed onto the particles to wet them uniformly. The wet mixture is dried at 40° to 50° C. to form granules. The granules are scattered over a noxious insert, and/or its habitat or the locus of its occurrence.

EXAMPLE 16

(oil preparation)

Compound No. 1 of this invention (0.5 part) and 99.5 parts of kerosene are mixed and stirred to form an oil preparation. It is sprayed onto a noxious insect, mite or nematode and/or its habitat or the locus of its occurrence.

EXAMPLE 17

(biological test)

Test on *Nephotettix cincticeps* having resistance to organophosphorus agents:

Preparation of a test chemical

Solvent: 3 parts by weight of xylene
Emulsifier: 1 part by weight of polyoxyethylene alkyl phenyl ether To form a suitable preparation, 1 part by weight of the active compound was mixed with the aforesaid amount of the solvent contaning the aforesaid amount of the emulsifier. The mixture was diluted with water to a predetermined concentration.

Testing method

Onto rice plants, about 10 cm tall, planted in pots each having a diameter of 12 cm was sprayed 10 ml per pot of the water-dilution of each active compound in a predetermined concentration prepared as above. The sprayed chemical was dried, and a wire net having a diameter of 7 cm and a height of 14 cm was put over each pot, and 30 female imagoes of *Nephotettix cincticeps* showing resistance to organophosphorus agents were released into the net. The pots were each placed in a constant temperature chamber and the number of dead insects was examined 2 days later, and the kill ratio was calculated.

The results are shown in Table 5.

TABLE 5

| Compound No. | Concentration of the active ingredient (ppm) | Kill ratio (%) |
|---|---|---|
| 1 | 8 | 100 |
| 9 | 8 | 100 |
| 13 | 8 | 100 |
| 14 | 8 | 100 |
| 22 | 8 | 100 |
| 24 | 8 | 100 |
| 29 | 8 | 100 |
| 95 | 8 | 100 |
| 97 | 8 | 100 |
| Comparison | | |
| A-1 | 40 | 65 |
| B-1 | 40 | 55 |

Note
[1]The compound numbers are the same as given above.
[2]Comparisons A-1 and B-1 were of the following structures:

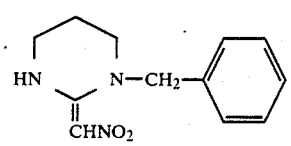

(A-1)

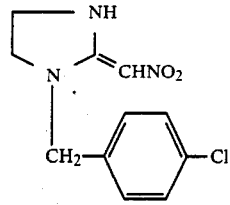

(B-1)

In addition to the compounds exemplified in Example 17, for example, Compound Nos. 48, 49, 50, 51, 55, 96 and 98 also showed excellent insecticidal effects in the same test as Example 17.

EXAMPLE 18

(biological test)

Test on planthoppers:

Testing method

A water dilution in a predetermined concentration of the active compound prepared as in Example 17 was sprayed onto rice plants, about 10 cm tall, grown in pots with a diameter of 12 cm in an amount of 10 ml per pot. The sprayed chemical was dried, and a wire net, 7 cm in diameter and 14 cm tall, was put over each of the pots. Thirty female imagoes of *Nilaparvata lugens* Stal of a strain which showed resistance to organophosphorus chemicals were released into the net. The pots were left to stand in a constant temperature chamber and the number of dead insects was examined two days later. The kill ratio was then calculated.

In the same way as above, the kill ratio was calculated on *Sogatella furcifera* Horvath and organophosphorus-resistant *Laodelphax striatellus* Fallen.

The results are shown in Table 6.

TABLE 6

| Compound No. | Concentration of the active ingredient (ppm) | Kill ratio (%) | | |
|---|---|---|---|---|
| | | N. lugens | L. striatellus | S. furcifera |
| 1 | 40 | 100 | 100 | 100 |
| 7 | 40 | 100 | 100 | 100 |
| 9 | 40 | 100 | 100 | 100 |
| 13 | 40 | 100 | 100 | 100 |
| 14 | 40 | 100 | 100 | 100 |
| 29 | 40 | 100 | 100 | 100 |
| 50 | 40 | 100 | 100 | 100 |
| 95 | 40 | 100 | 100 | 100 |
| 97 | 40 | 100 | 100 | 100 |
| Comparison | | | | |
| A-1 | 40 | 50 | 40 | 40 |
| B-1 | 40 | 30 | 30 | 30 |

Note:
[1]The compound numbers are the same as above.
[2]Comparisons A-1 and B-1 are the same as in the footnote to table 5.

EXAMPLE 19

(biological test)

Test on *Myzus persicae* (green peach aphids) having resistance to organophosphorus chemicals and carbamate chemicals:

Testing method

Green peach aphids which had been bred and had resistance to organophosphorus chemicals and carbamate chemicals were inoculated on eggplant seedlings (black elongate eggplants), about 20 cm tall, grown in unglazed pots having a diameter of 15 cm (about 200 aphids per seedling). One day after the inoculation, a water dilution of each active compound at a predetermined concentration prepared as in Example 17 was sprayed in a sufficient amount onto the plants using a spray gun. After the spraying, the pots were left to stand in a greenhouse at 28° C. Twenty-four hours after the spraying, the kill ratio was calculated. For each compound, the test was carried out through two replicates.

The results are shown in Table 7.

TABLE 7

| Compound No. | Concentration of the active ingredient (ppm) | Kill ratio (%) |
|---|---|---|
| 1 | 200 | 100 |
| 9 | 200 | 100 |
| 13 | 200 | 100 |
| 14 | 200 | 100 |
| 25 | 200 | 100 |
| 30 | 200 | 100 |
| 95 | 200 | 100 |
| 97 | 200 | 100 |
| Comparison | | |
| A-1 | 1000 | 80 |
|  | 200 | 30 |
| B-1 | 1000 | 60 |
|  | 200 | 10 |
| Estox (commercial product) | 1000 | 100 |
|  | 200 | 20 |

Note:
[1]The compound numbers and comparisons A-1 and B-1 are the same as above.
[2]Estox: S—2-ethylsulfinyl-1-methylethyldimethyl-phosphorothiolate (45% emulsifiable concentrate).

It will be understood that the specification and examples are illustrative but not limitative of the present invention and that other embodiments within the spirit and scope of the invention will suggest themselves to those skilled in the art.

We claim:

1. A nitromethylene derivative of the formula

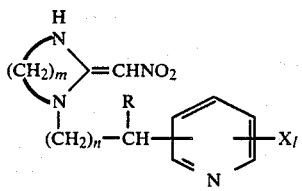

in which
R is a hydrogen atom or an alkyl group with 1 to 4 carbon atoms,
X is a halogen atom; a lower alkyl, lower alkoxy, lower alkylthio, lower alkylsulfinyl, lower alkylsulfonyl or lower alkenyl group with up to 6 carbon atoms; a lower alkynyl group with up to 4 carbon atoms; a phenyl, phenoxy, phenylthio, naphthyl, naphthoxy or naphthylthio group which may optionally be substituted by halogen; or a benzyl, phenethyl or naphthylmethyl group,
l is 1, 2, 3 or 4,
m is 3, and
n is 0, 1, 2 or 3,
or a salt thereof.

2. A nitromethylene derivative or salt thereof according to claim 1, wherein m is 3.

3. A compound according to claim 1, wherein such compound is 1-(2-chloro-5-pyridylmethyl)-2-(nitromethylene)tetrahydropyrimidine of the formula

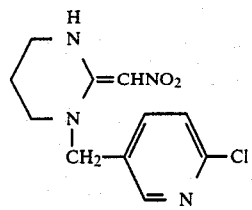

or a salt thereof.

4. A compound according to claim 1, wherein such compound is 1-2-(fluoro-5-pyridylmethyl)-2-(nitromethylene)tetrahydropyrimidine of the formula

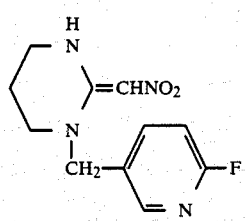

or a salt thereof.

5. A compound according to claim 1, wherein such compound is 1-(2-bromo-5-pyridylmethyl)-2-(nitromethylene)tetrahydropyrimidine of the formula

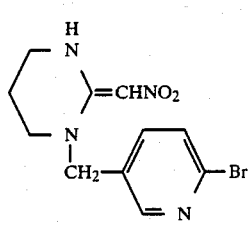

or a salt thereof.

6. A compound according to claim 1, wherein such compound is 1-(2-methyl-5-pyridylmethyl)-2-(nitromethylene)tetrahydropyrimidine of the formula

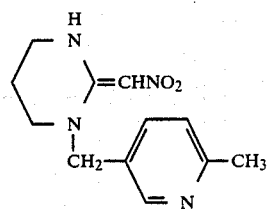

or a salt thereof.

7. An insecticidal composition comprising an insecticidally effective amount of a compound or salt according to claim 1 in admixture with a diluent.

8. A method of combating insects which comprises applying to such insects or a habitat thereof an insecticidally effective amount of a compound or salt according to claim 1.

9. The method according to claim 8, wherein such compound is 1-(2-chloro-5-pyridylmethyl)-2-(nitromethylene)tetrahydropyrimidine, 1-2-(fluoro-5-pyridylmethyl)-2-(nitromethylene)tetrahydropyrimidine, 1-(2-bromo-5-pyridylmethyl)-2-(nitromethylene)tetrahydropyrimidine, or
1-(2-methyl-5-pyridylmethyl)-2-(nitromethylene)tetrahydropyrimidine,
or a salt thereof.

* * * * *

UNITED STATES PATENT AND TRADEMARK OFFICE
CERTIFICATE OF CORRECTION

PATENT NO. : 4,774,247
DATED : September 27, 1988
INVENTOR(S) : Kozo Shiokawa, et al It is certified that error appears in the above-identified patent and that said Letters Patent is hereby corrected as shown below:

Col. 2, line 53  After "$R_2$-" delete "$R_2$" and substitute --$R_3$--

Col. 21, line 5  After example "1b:" delete "$H_5CO$" and substitute --$H_3CO$--

Col. 21, line 44  After example "1c:" delete "$H_5CO$" and substitute --$H_3CO$--

Col. 24, line 13  After compound 22 insert:

| --Comp.# | m | n | R | Pyridine-bonded position | x1 | m.p. |
|---|---|---|---|---|---|---|
| 23 | 3 | 0 | H | 5 position | 2-$CH_3$ | mp. 138–140°C-- |

Col. 28, line 61  After "noxious" delete "insert" and substitute --insect--

Signed and Sealed this

Fifth Day of September, 1989

Attest:

DONALD J. QUIGG

Attesting Officer

Commissioner of Patents and Trademarks